United States Patent [19]

Scholz et al.

[11] 4,305,733
[45] Dec. 15, 1981

[54] METHOD OF TREATING NATURAL GAS TO OBTAIN A METHANE RICH FUEL GAS

[75] Inventors: Walter Scholz, Wolfratshausen; Gerhard Ranke, Pöcking; Hans Becker, Munich, all of Fed. Rep. of Germany; Boris G. Bergo, Moscow, U.S.S.R.; Alexander I. Grizenko, Moscow, U.S.S.R.; Alexej V. Frolov, Moscow, U.S.S.R.

[73] Assignees: Linde AG, Wiesbaden, Fed. Rep. of Germany; Vniigaz, Gorod, U.S.S.R.

[21] Appl. No.: 127,886

[22] Filed: Mar. 6, 1980

[30] Foreign Application Priority Data

Mar. 9, 1979 [DE] Fed. Rep. of Germany ....... 2909335

[51] Int. Cl.³ .............................................. C10L 3/00
[52] U.S. Cl. .................................. 48/196 R; 62/17; 62/24; 62/27; 55/68; 55/73
[58] Field of Search .............. 48/196 R; 62/17, 20, 62/24, 27, 28; 55/68, 73

[56] References Cited

U.S. PATENT DOCUMENTS

| | | | |
|---|---|---|---|
| 1,429,175 | 9/1922 | Thompson | 48/196 R |
| 2,886,611 | 5/1959 | King et al. | 62/17 |
| 3,210,949 | 10/1965 | Wienecke | 62/17 |
| 3,531,917 | 10/1970 | Grunewald et al. | 55/73 |
| 3,710,546 | 1/1973 | Grunewald et al. | 55/73 |
| 3,770,622 | 11/1973 | Freirerl et al. | 55/68 |
| 3,977,203 | 8/1976 | Hinton et al. | 62/20 |
| 4,070,165 | 1/1978 | Colton | 62/17 |
| 4,097,250 | 6/1978 | Pogani et al. | 55/73 |

*Primary Examiner*—Peter F. Kratz
*Attorney, Agent, or Firm*—Karl F. Ross

[57] ABSTRACT

A method for the recovery of a methane-rich natural gas from a natural gas containing, apart from methane, also hydrogen sulfide, carbondioxide, higher hydrocarbons and, in most cases, organosulfur compounds. According to the invention a hydrocarbon fraction of $C_4$ hydrocarbons and higher is naturally removed from the natural gas which is then subjected to a selective scrubbing for the removal of hydrogen sulfide with a regeneratable extraction, of scrubbing liquid. Next a $C_3$ fraction is removed, the remaining gas being scrubbed with a second regeneratable washing agent, for the removal of carbondioxide to leave the methane-rich gas.

18 Claims, 2 Drawing Figures

METHOD OF TREATING NATURAL GAS TO OBTAIN A METHANE RICH FUEL GAS

FIELD OF THE INVENTION

Our present invention relates to a method of and to an apparatus for the separation of natural gas into components thereof and, more particularly, to a method of and an apparatus for the recovery of a methane-rich fraction from natural gas, substantially free from $C_3$ or higher hydrocarbon compounds, hydrogen sulfide and carbon dioxide.

BACKGROUND OF THE INVENTION

Natural gas in recent years has been playing an increasingly important role as an energy source for industrial and building-heating applications, in the generation of electric power and in many other cases. The natural gas as recovered from the ground comprises, in addition to methane, several percent by volume of higher hydrocarbons.

It is frequently desirable to recover these higher hydrocarbons either for use in the synthesis of still other organic compounds or for collection of a $C_3/C_4$ fraction which can be recovered as a liquid and can be used as liquefied gas for various industrial and commercial applications, e.g. as the fuel for cigarette lighters, household appliances, torches or the like.

In addition, the natural gas contains significant quantities of sulfur compounds, usually in the form of hydrogen sulfide ($H_2S$) and carbonyl sulfide (COS), as well as carbon dioxide ($CO_2$) in an amount up to 20%. Present in the natural gas may also be organosulphur compounds such as mercaptans, which can also be considered higher hydrocarbons because they generally have a carbon count of three or more.

It is generally considered advantageous, usually essential, to remove the $H_2S$, COS and $CO_2$ from the natural gas to leave a methane-rich component which is delivered for use in the industry, power plant, chemical and heating operations mentioned previously.

While there are many reasons for this requirement, it can be readily appreciated that carbon dioxide, if present in the methane-rich gas, acts as a diluent which contributes no useful energy and merely increases the volume of the gas which must be processed or handled. Its presence, therefore, calls for an increase in the size of the apparatus, e.g. boiler, burners and pipelines, for a given generation of heat and thus increases the cost of the plant utilizing the natural gas. In fact, it functions as an agent reducing the heat value of the natural gas.

Furthermore, removal of the $CO_2$ can contribute advantages on other levels, since the carbon dioxide in relatively pure compressed or solid form, is itself a valuable commodity which can be used for many purposes, e.g. the production of dry ice, as a participant in reactions in which carbon dioxide is necessary, etc.

It is equally obvious that hydrogen sulfide must be removed from the natural gas before it is used as a fuel to avoid high sulfide dioxide levels in the combustion of exhaust gases with the concomitant detriment to the environment and the combustion apparatus. On the other side hydrogen sulfide is a valuable product which can be used for the production of elemental sulfur. The same holds true for the carbonoxysulfide or carbonyl sulfide (COS).

It is known to remove hydrogen sulfide and carbon dioxide from natural gas by subjecting the latter in successive stages to scrubbing operations.

The scrubbing solution used in the first stage is a liquid which is partially charged with $CO_2$ and which preferentially scrubs $H_2S$ from the natural gas. This liquid is then subjected to complete regeneration and is used to scrub $CO_2$ out of the gas in the second stage, thereby being partly charged with $CO_2$ and adapted to be used in the first stage.

This system has the disadvantage that both the said gas components, namely $H_2S$ and $CO_2$ are collected in a single scrubbing solution, thereby complicating the regenerating process if the two are to be recovered independently.

The regeneration cost is significant and with conventional processes it is not generally possible to recover the two acid gas components individually with high purity, nor is a recovery of higher carbons possible.

OBJECTS OF THE INVENTION

It is the principal object of the present invention to provide an improved method of removing impurities from natural gas so as to produce a methane-rich product, whereby the disadvantages of earlier systems are obviated.

Another object of the invention is to provide an improved method of separating components such as higher hydrocarbons, hydrogen sulfide and carbon dioxide from a natural gas so that the substances can be recovered in higher purity and/or in a more commercially useful form.

Yet another object is to provide an improved apparatus for carrying out the method of the present invention at minimum cost.

SUMMARY OF THE INVENTION

These objects, and others which will become apparent hereinafter, are attained in accordance with the present invention which utilizes a process wherein the natural gas, generally at a significant wellhead pressure, is subjected to a first removal of high hydrocarbons having a carbon number of 4 or more ($C_{4+}$ hydrocarbons), the gas thereafter being scrubbed with a first regeneratable scrubbing liquid capable of solubilization of the hydrogen sulfide. The gas, from which the hydrogen sulfide has been removed is then subjected to a second hydrocarbon separation in which $C_3$ hydrocarbons are recovered and is thereafter scrubbed with a second regeneratable liquid capable of solubilizing carbon dioxide, the resulting gas (from which carbon dioxide has been removed) being the methane-containing product.

Our invention is based upon the discovery that the higher hydrocarbons, being highly soluble in the physically acting scrubbing liquids, tend to create problems in the separation of the hydrocarbons from the scrubbing solutions during the regeneration, and usually cannot even be fully recovered. Furthermore, they appear to obstruct the scrubbing-efficiency with respect to the acid gases and, if driven off with the acid gases, are difficult to separate from them because of the relatively small difference between the boiling point of the acid gases and, for example, the $C_3$ hydrocarbons.

Surprisingly, we have found that the initial removal of the $C_{4+}$-hydrocarbon fraction and the use of individual scrubbing liquids in two distinct scrubbing operations separated by hydrocarbon removal, permits a practically quantitative recovery of the higher hydrocarbons, hydrogen sulfide and carbonyl sulfide, and carbon dioxide without the detrimental interplay previously mentioned. Concern over separation of the acid gases and the higher hydrocarbons from the acid gases, as is the case when a single scrubbing solution is used even in two successive stages or in a single stage, is eliminated.

According to another feature of the invention, a considerable energy saving is gained by separating out at least the $C_4$ and higher hydrocarbons initially utilizing a step which involves the cooling of the gas. Since the gases are at a relatively elevated wellhead pressure cooling can be effected simply by expansion to lower pressures with dewpoint separation or condensation, or rectification.

Thus the separation of the high hydrocarbons from the raw natural gas is not effected in a single step, but rather in two successive steps, each time directly or immediately before a scrubbing stage. The cold energy required for condensation of the higher hydrocarbons can be obtained exclusively or in major part by expansion in the manner described. For example, in the first separating stage, the raw natural gases expand and thereby cool to a temperature sufficient to enable $C_4$ and higher hydrocarbons to condense from the gas. If any additional energy consumption for cooling is required it is minimal when the raw gas is initially at the wellhead pressure. The separation of the $C_4$ and higher hydrocarbons can thus be effected either in simple separators by condensation or with the aid of conventionally designed rectification columns (see chapter 12, pp. 12 ff. of Perry's chemical Engineers' Handbook, McGraw-Hill Book Co., N.Y. 1963).

When rectification columns are used, the separation can be carried out in the main cycle or in an auxiliary or secondary cycle.

In order to prevent the separation of solid gas hydrates, e.g. $CO_2.xH_2O$ or $C_nH_{2n+2}.xH_2O$, which can plug the apparatus, it has been found to be advantageous to add methanol to the gas especially when the process is to be carried out in a rectification column.

The addition of a sufficient quantity of anhydrous methanol to thoroughly dry the gas has the further advantage that it is capable of reducing the water content of the final product to the maximum which is permissible upon supply of the verified methane to a pipeline.

While the use of a separator to remove the solid gas hydrates is less expensive, such separators cannot reduce the moisture content in the gas to the desired low level so that additional stages must be provided for this purpose.

The gas thus freed from the $C_{4+}$ hydrocarbons is then subjected in a washing column or scrubbing tower to contact with a scrubbing agent capable of removing hydrogen sulfide.

Considering the fact that the gas, dried by methanol and passing through the rectification column should remain waterfree even after the hydrogen sulfide and carbon dioxide scrubbing steps, the scrubbing agent in each of these stages is waterfree according to the principles of the present invention.

We have found that organic scrubbing agents specific to hydrogen sulfide, such as toluene, N-methylpyrrolidone, dimethylformamide, isopropanolamine and especially dialkyl ethers of diethylene glycols and especially the dimethyl ethers of di- to heptaethylene glycols are suitable. Highly effective results are also obtained with dimethylisopropyl ethers of ethylene glycols. Unless otherwise stated, the term "alkyl" will mean $C_1$ to $C_{18}$ straight or branched chain hydrocarbons and corresponding cycloalkyl compounds.

In principle, hydrogen sulfide-selective water-based solvents can also be used, for example aqueous solutions of aminoacid salts, although these scrubbing agents must be employed at temperatures above their respective freezing points and additional stages must be provided to dry the gas.

The gas thus freed from hydrogen sulfide is subjected to a further cooling to quantitatively separate out the $C_3$ hydrocarbons as much as possible. The reduction of the temperature of the gas to effect a dewpoint separation of the $C_3$ hydrocarbons can be done economically because the gas is generally still at a sufficiently elevated pressure to bring about the temperature reduction by simple expansion. This separation can also be carried out in simple condensers or rectification columns.

According to another aspect of the invention, the separation of the $C_3$ hydrocarbons is not carried out by cooling and condensation, but rather by scrubbing the gas with still another (third) scrubbing agent selective as to the $C_3$ hydrocarbons. This latter alternative is employed when only small proportions of $C_3$ hydrocarbons are present since, in such cases, the condensation can only be carried out with difficulty and is energetically costly requiring extremely low temperatures.

When a solvent-type scrubbing is desired to remove the $C_3$-hydrocarbons, the scrubbing agent is preferably a mixture of $C_7$ to $C_{11}$ hydrocarbons, e.g. a gasoline cut obtained elsewhere in the plant. Toluene can also be used for this purpose. These scrubbing agents have, apart from the ability to solubilize the $C_3$-hydrocarbons, the surprising advantage of being able to pick up any hydrogen sulfide which may have survived in the gas following the first scrubbing step, and any COS which may be present, thereby preventing such sulfur compounds from interfering with the $CO_2$ cutting step to follow. This is especially important when high purity $CO_2$ is desired, especially for use in the food industry.

It should be noted that the quantity of the third scrubbing agent which is necessary in this variant of the process is relatively small since the removal of the $C_3$-hydrocarbons and carbonyl sulfide can be effected with relatively small quantities. Nevertheless, the minimum amount required for this purpose should be used and, in the case of condensation separation, the temperature should only be dropped enough to obtain the desired degree of separation of the $C_3$-hydrocarbons.

The scrubbing of the $C_3$-hydrocarbons and the COS from the gas following the $H_2S$ scrubbing operation is independent of the critical pressure of the gas so that the process can be carried out at relatively high pressures without difficulty. This is especially significant when the raw gas is derived from wells under significant wellhead pressures and the cleaning operation in total can be carried out at an elevated pressure and without unnecessary expansion of the gas. This eliminates the need to recompress the verified gas before it is fed to the pipeline, thereby affording still another saving in energy.

Following the separation of the $C_3$-hydrocarbons and the COS from the gas, the latter is scrubbed with the second scrubbing agent for the specific removal of $CO_2$. To avoid increasing the moisture content of the gas, we prefer to operate at this stage with a physical solvent, generally an organic solvent of carbon dioxide, for example N-methylpyrrolidone and dimethylformamide, ketones and alcohols, for example methanol, which have significant capabilities for solubilizing $CO_2$ at low temperatures, being also highly selective and easily regeneratable.

From the head of the scrubbing tower in this stage, we derive a gas consisting predominantly of methane and free of the impurities mentioned previously, which meets pipeline specifications and can be delivered to the consumer.

According to a further feature of the invention, the scrubbing agent from the first or $H_2S$ scrubbing operation and any scrubbing agent from the third scrubbing stage in which $C_3$-hydrocarbons and COS are preferentially removed from the gas, are each expanded and the respective gas phases are treated in afterscrubbers with a small portion of the respective pure washing agent to be used in the main washing or scrubbing column.

This mode of operation has been found to be highly advantageous.

Physically effective scrubbing agents, of the type preferred in accordance with the present invention, also tend to solubilize other components from the gas and, at elevated pressures, these compounds are solubilized to an even greater extent. Since such cold solubilized components reduce the quality of the scrubbed product, i.e. solubilized hydrocarbons interfere with the conversion of $H_2S$ to elemental sulfur by the Claus process, the afterscrubbing treatment described above has been found to be particularly advantageous.

Of course, after the expansion of the charged scrubbing agent, the freed gases can be compressed and returned to the raw natural gas to be removed from the scrubbing agent without loss, increases the concentration of recoverable components in the raw gas and the effectiveness of the stage in which these components are removed, and requires only a relatively small energy consumption for compressing while only limitedly increasing the loading of the scrubbing stages.

According to the invention, however, this procedure need not be used if the gases released by the expansion are contacted with pure scrubbing agents in the afterscrubbing process mentioned previously, the gas from the first afterscrubber being passed into a second afterscrubber and thereafter combined with expansion gases from the charged second scrubbing agent. The combined gas can be compressed and scrubbed together with the gas from the third main scrubbing stage, in the second main scrubber.

This process has the advantage that the desirable gas components, namely $CH_4$, $H_2S$ and $CO_2$ are removed substantially in pure form without significant ballast gases, for example other hydrocarbons, being recycled through the entire apparatus.

For regeneration, the combined scrubbing agents of the third main scrubber and the second afterscrubber are initially passed through a low pressure regenerating column with some heating and head cooling. From the latter the regenerated third scrubbing agent is directly introduced into the third main scrubber and the second afterscrubber.

From the head of the latter regenerating column, a gas containing $CO_2$, COS and $C_3$-hydrocarbons is withdrawn and, after compression, is rectified into a $C_3$-hydrocarbon fraction and a $CO_2$ fraction, the COS being found primarily in the $C_3$ fraction.

The latter fraction, together with the higher hydrocarbons, is subjected to hydrogenation and separation of $H_2S$ to form a $C_{3+}$ hydrocarbon fraction which is free from sulfur. Hydrogen sulfide and residual hydrocarbons are returned to the main process.

The regeneration of the first and second scrubbing agents and the recovery of pure $CO_2$ from the second scrubbing agent are carried out by methods known in the art and which need not be discussed in detail here.

Among the advantages of the process of the present invention is that the higher hydrocarbons as well as the individual acid gas components $CO_2$ and $H_2S$ can be removed separately from the natural gas and are recovered separately in a substantially more convenient and economical manner than has been possible heretofore and in greater purity or in such a form as to allow more economical utilization. The hydrogen sulfide recovered from the first scrubbing process and freed from the regeneration of its scrubbing agent, is practically free from hydrocarbons and is recovered at a substantial concentration and amount so that it can be used directly in a Claus apparatus for the production of elemental sulfur.

Similarly, the carbon dioxide which is released from the scrubbing agent of the second scrubbing stage, has a high concentration which allows liquefaction, after a fine purification, and use as technically pure or food grade carbon dioxide in commerce.

The rectification or solvent-scrubbing third stage of the process, between the two scrubbing stages for the removal of the acid gases, effective for the complete recovery of the $C_3$-hydrocarbons, involves a fine separation of residual $H_2S$ and organosulfur compounds.

Since pipeline specifications for natural gas do not generally limit the $CO_2$ content thereof to the same degree that other components are excluded, it is a further feature of the invention to permit the regeneration of the second scrubbing agent to remain somewhat incomplete upon recirculation to the scrubbing process. This allows a further saving in energy, bearing in mind that energy consumption increases with increasing purity of the scrubbing agent.

BRIEF DESCRIPTION OF THE DRAWING

The above and other objects, features and advantages of the present invention will become more readily apparent from the following description, reference being made to the accompanying drawing in which.

SPECIFIC DESCRIPTION AND EXAMPLE

Figure 1:
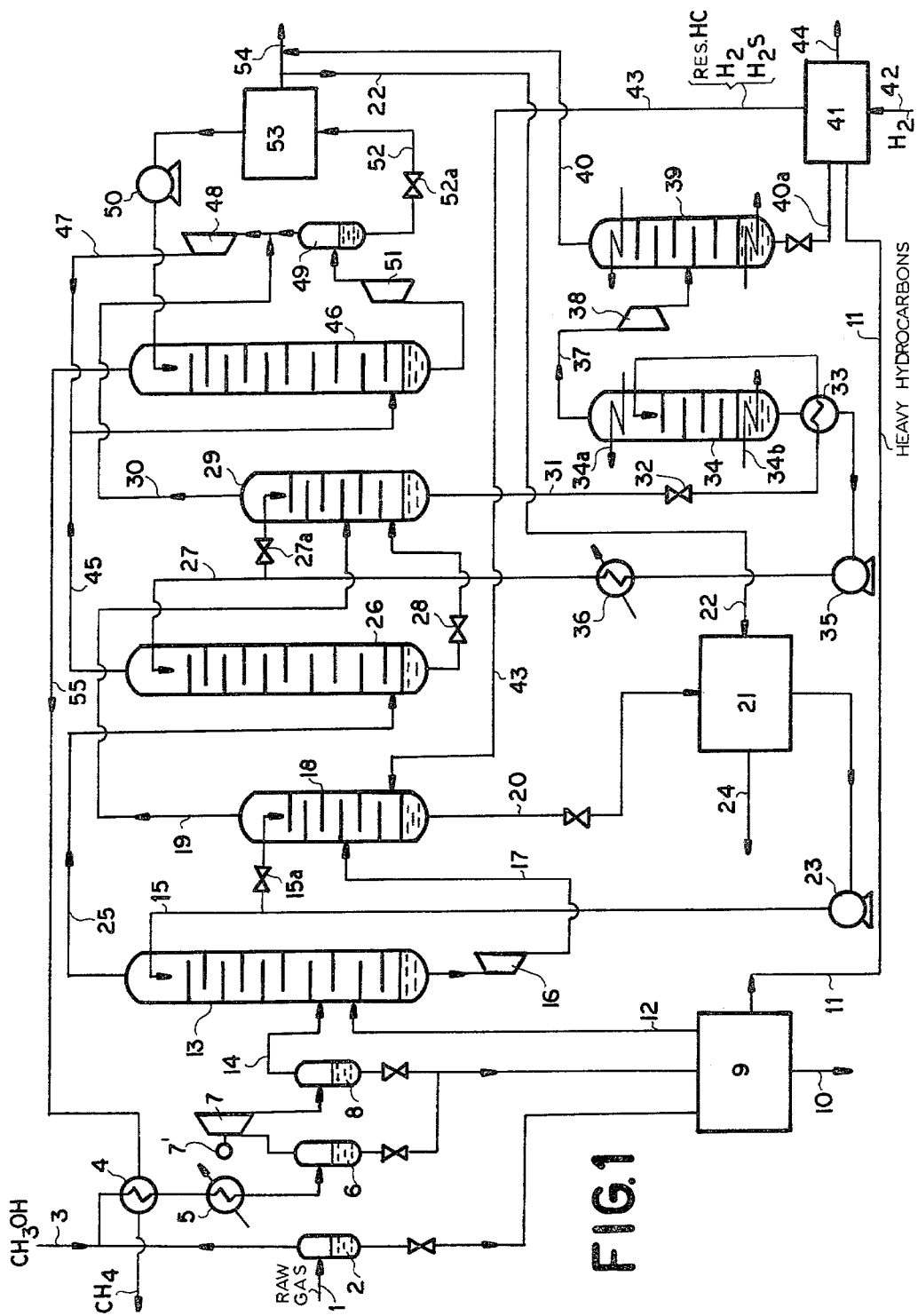
FIG. 1 is a flow diagram of a plant for the separation of raw natural gas in accordance with the principles of the present invention using a scrubbing step to extract the $C_3$-hydrocarbons and COS from the gas.

The following description of the plants illustrating two embodiments of the invention are given with numerical values of various parameters by way of example for the first embodiment. Thus the entire description of the first plant constitutes a specific example as to the operation thereof.

EXAMPLE AND DESCRIPTION OF FIG. 1.

A pipe 1 delivers a raw natural gas at a rate of 100 kmol/h at a wellhead pressure of 85 bar and at a temperature of 30° C. to the system. The gas has the following composition:

| | | |
|---|---|---|
| $N_2$ | | 1.98 kmol/h |
| $CH_4$ | Hydrocarbons | 47.48 kmol/h |
| $C_2$ | Hydrocarbons | 1.92 kmol/h |
| $C_3$ | Hydrocarbons | 0.93 kmol/h |
| $C_4$ | Hydrocarbons | 0.56 kmol/h |
| $C_{5+}$ | Hydrocarbons | 3.08 kmol/h |
| $H_2S$ + | org. S. Compounds | 22.50 kmol/h |
| $CO_2$ | | 21.55 kmol/h |

Since the raw gas entrains liquids, these are initially removed by conventional liquid gas separation techniques in the separator schematically shown at 2.

Line 3 delivers 0.1 kmol/h methanol to the gas leaving the separator 2 and the resulting mixture is passed through a heat exchanger 4 and is there cooled in indirect heat exchange with product gas. The partially cooled raw gas then traverses a heat exchanger 5 in which it can be cooled further by another coolant in an energy-consuming cycle so that the temperature of the gas leaving the heat exchanger 5 is about −10° C.

The condensate formed in the gas as a result of this cooling is collected in a liquid/gas separator 6, the gas phase being expanded in an expansion turbine 7 which can be coupled to an electric generator 7' so that the work expansion of the gas produces usable energy while cooling the gas. The output pressure of the turbine is about 60 bar and condensate formed by the cooling which results from the expansion is collected in a liquid/gas separator 8.

Under the conditions described, all of the water in the natural gas is collected in the separators 2, 6 and 8.

The higher hydrocarbons of a carbon number of four or more and acid gases also are collected in the separators.

The collected condensate is processed as represented schematically at 9 by any conventional procedure, e.g. by separating the water/methanol phase from the hydrocarbon phase (decantation) and the separating of the hydrocarbon phase to its components by reflux condensation (fractionation) or rectification. The water/methanol phase is discharged at 10 to a separator which can free the methanol from the water, e.g. by distillation.

The heavy hydrocarbons are led away, as represented by line 11 for a purpose to be described subsequently.

The lighter hydrocarbons, with a carbon number up to $C_3$, are fed as represented by line 12 into a first scrubbing column 13 which also receives the gas from separator 8, i.e. raw gas from which readily condensable impurities and $C_{4+}$ hydrocarbons have been removed (line 14).

The gas in line 12 has a temperature of + 22° C. whereas that supplied by line 14 has a temperature of −25° C.

In the scrubbing tower 13, the gas is scrubbed with 2.2. metric tons/h of a scrubbing agent capable of selectively solubilizing hydrogen sulfide. In this example, the scrubbing agent is the dimethylisopropyl ether of ethylene glycol.

The scrubbing agent sprayed into the tower is at a temperature of −10° C. and the tower can be equipped with bubble plates, packing or the like to increase the contact efficiency between the scrubbing agent and the gas. Practically all of the hydrogen sulfide is solubilized in the recirculating scrubbing agent in this manner.

The charged scrubbing liquid is withdrawn from the sump of the column 13 and is expanded in a liquid turbine 16 to a pressure of 30 bar, the liquid being passed to a first after-scrubber 18. The gases released by the expansion or depressurization of the sump liquid are scrubbed in the tower 18 with 0.25 tons/h of the pure first scrubbing agent as controlled, for example, by a valve 15a. Any hydrogen sulfide which is solubilized in this manner is thus returned to the liquid phase in the sump from which the first scrubbing agent is withdrawn. The light low molecular weight hydrocarbons which are entrained in the liquid and are released by the expansion thereof, in an amount of about 3.03 kmol/h and free from $H_2S$, are drawn via line 19 from the head of the after-scrubber 18.

The sump liquid from the after-scrubber 18, at a temperature of +27° C., is drawn off and is fed as schematically represented by line 20 to a regenerating station 21 operating at relatively low pressure (for example, 2 bar). A stripping gas is fed to this unit as represented by line 22 and heat is supplied in the usual manner to regenerate the scrubbing liquid which can be recirculated by the pump 23 to the column 13. The pump 23 is dimensioned to build up the pressure in the recirculated scrubbing liquid to that prevailing in the tower 13, i.e. to 60 bar.

The residual gas at line 24 consists of hydrogen sulfide and carbon oxide which can be fed to a Claus plant for the production of elemental sulfur.

The gas freed from $H_2S$ in column 13 is passed via line 25 to a third scrubber 26 which operates at a pressure of 59 bar. The solvent used in this scrubber is 0.93 tons/h of a $C_7$ to $C_{11}$ hydrocarbon mixture at a temperature of −35° C., this extracting liquid being delivered by line 27.

A temperature at the head of the scrubbing column 26 of about −20° C. develops under these conditions and $C_3$ hydrocarbons are scrubbed from the gas together with other sulfur compounds such as carbonyl sulfide.

The charged third scrubbing agent is then expanded through a throttle 28 to a pressure of 30 bar and cooled as it is fed to a second after-scrubber 29.

The gas released by the expansion through the throttle 28 is scrubbed with a portion of third scrubbing agent in an amount of 0.27 tons/h at the column pressure. In addition, the after-scrubber 29 is supplied with 3.03 kmol/h of the head product of the scrubber 18 via line 19. In the after-scrubber 29, the rising gas mixture is completely freed from $C_3$-hydrocarbons and COS by the scrubbing operation and 7.44 kmol/h of gas is withdrawn via line 30.

The charged washing agent from the after-scrubber 29 is withdrawn from the sump at 31 and is expanded through a throttle 32 to a pressure of 3 bar, then heated in a heat exchanger 33, and supplied to a regenerating column 34.

The regenerating column 34 is provided with a head-cooling or refluxing unit 34a and a sump-heating or boiling unit 34b.

The regenerated third scrubbing agent is recovered from the sump of the column 34 at a temperature of +200° C., passes through the heat exchanger 33 and is thereby cooled, is displaced via a pump 35 capable of generating a pressure of 59 bar, passed through an aftercooler or exchanger 36 which lowers its temperature to −35° C. with the aid of a foreign coolant source, and delivered via line 27 to the head of the washing tower 26, a small portion being shunted via valve 27a from the line 27 to the head of the second after-scrubber 29.

A gas is withdrawn via line 37 from the head of the regenerating column 34 which consists substantially of $C_3$ hydrocarbons, $CO_2$ and COS, this gas being compressed to 30 bar by the compressor 38 before being introduced at this pressure into a rectification column 39.

The rectification column 39 is supplied with sump-heating and head-cooling units as described for the column 34 previously. The head product of this column is $CO_2$-rich gas at a temperature of $-14°$ C. which is withdrawn via line 40.

The sump product of the rectification column 39 consists substantially of $C_3$ hydrocarbons and COS and is withdrawn at a temperature of $+77°$ C., being supplied via line 40a to a hydrogenation and $H_2S$-separation unit 41. This unit, shown only schematically, is also supplied with heavy hydrocarbons and hydrogen via lines 11 and 42, respectively, the heavy hydrocarbons having been recovered from the unit 9 as previously described.

The gas withdrawn at 43 consists essentially of hydrogen sulfide and residual light hydrocarbons and is recycled to the lower portion of the first after-scrubber 18.

The gas withdrawn from line 44 has the following composition:

| | | |
|---|---|---|
| $C_2$ | Hydrocarbons | 0.02 kmol/h |
| $C_3$ | Hydrocarbons | 0.81 kmol/h |
| $C_4$ | Hydrocarbons | 0.53 kmol/h |
| $C_{5+}$ | Hydrocarbons | 3.08 kmol/h |

The gaseous head product of the third washing column 26 is delivered by line 45 to the lower portion of the second washing column or tower 46 and is mixed with 19.34 kmol/h of a gas fed via line 47 from the compressor 48 at a pressure of 58 bar and formed from the head product gases of the second after-scrubber 29 (line 30) and expansion gases from a separator 49.

In the second scrubbing column 46, the gas is scrubbed with 3 tons/h of methanol at a temperature of $-50°$ C., the methanol being delivered to the tower by the pump 50 and being sprayed into the head of the column. Upon trickling past the bottoms, plates or packings of the scrubbing column 46, the methanol absorbs the carbon dioxide.

The charged second scrubbing liquid (methanol) is withdrawn from the sump of the column 46 and is expanded in the liquid turbine 51 to a pressure of 30 bar, the cooled and expanded product, at a temperature below the dewpoint, being separated in the liquid/gas separator 49.

The liquid phase is generally methanol-containing solubilized $CO_2$ while the gaseous phase consists of hydrocarbons solubilized in or entrained by the methanol. The gases, in an amount of 11.9 kmol/h are fed together with the head gas from the second afterscrubber 29, to the compressor 48.

The expanded methanol is fed through line 52 and an expansion valve 52a to a regenerating unit 53 in which the methanol is regenerated and dissolved $CO_2$ is removed.

Regenerated methanol is supplied by the pump 50 to the head of the second scrubber 46 while line 54 carries away a gas of the following composition:

| | |
|---|---|
| Methane | 0.4 kmol/h |
| $C_2$ Hydrocarbons | 0.19 kmol/h |
| $CO_2$ | 19.28 kmol/h |

A portion of carbon dioxide liberated in the unit 53 is branched off via line 52 and is fed to unit 51 as previously described as the stripping gas.

The carbon dioxide fraction in line 54 is combined with the head gas from the rectifier column 39 via line 40.

The head product of the scrubber 46 is a gas which is at a temperature of $-50°$ C. and consists predominantly of methane, i.e. is the purified natural gas which is passed through the heat exchanger 4 and has the following composition:

| | |
|---|---|
| $N_2$ | 1.96 kmol/h |
| Methane | 46.28 kmol/h |
| $C_2$ Hydrocarbons | 1.63 kmol/h |
| $CO_2$ | 0.12 kmol/h |

This product meets pipeline specifications and can be delivered to natural gas consumers directly or after further compression. It should be noted that it has no significant moisture content.

DESCRIPTION OF FIG. 2

Figure 2:
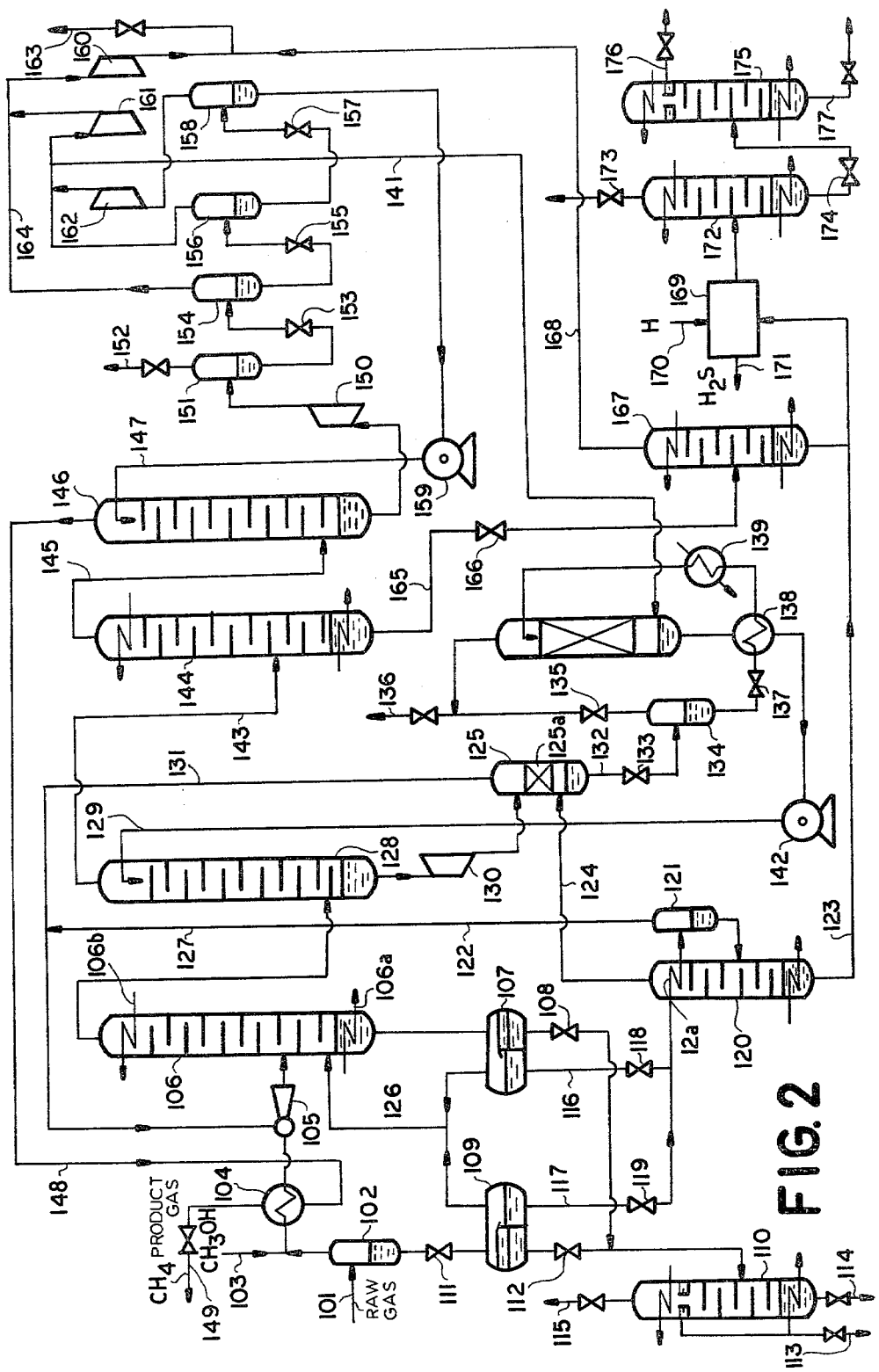
FIG. 2 is a flow diagram of a plant which is otherwise generally similar to that of FIG. 1 but which utilizes a condensation/rectification stage for the removal of $C_3$-hydrocarbons and the COS.

In the embodiment of FIG. 2, the raw natural gas is delivered via a line 101 and entrained liquids are removed in a liquid/gas separator 102. Methanol is added to the gas phase from the separator 102 and the mixture is passed to the heat exchanger 104 where it is subjected to indirect heat exchange with the product gas and cooled. The thus cooled raw gas is expanded in an ejector 105 which draws gas via line 131 from a separator 125 which will be described subsequently. The gas from line 131 has previously been compressed to the same pressure as the raw gas supplied to the ejector.

The gas mixture is introduced into a rectifier column 106 provided with a sump-heating coil 106a and a head-cooling or refluxing coil 106b. The sump product which collects in this column is a liquid mixture of $C_4$ hydrocarbons, higher hydrocarbons, small amounts of $C_3$ hydrocarbons, acid gas components, methanol and water. The mixture is fed to a decanter 107 which permits separate withdrawal of the aqueous and hydrocarbon phases.

The aqueous phase from the decanter 107 is expanded in a throttle valve 108 and is combined with the aqueous phase from a decanter 109 before being fed to rectifying column 110. The latter column is provided with a sump heater or boiler and a head cooler as previously described. The liquid in decanter 109 derives from the liquid phase or condensate withdrawn from the separator 102 and expanded in the throttle valve 111. The aqueous phase from the decanter 109, prior to combination with the aqueous phase of decanter 107, is expanded through the valve 112.

The sump-heated rectifying column 110 serves to separate water from methanol and to drive off solubilized gases. The methanol is removed as a head condensate via line 113 for further use while the water is withdrawn from the sump by line 114.

The released gases, containing hydrogen sulfide, are combined with the product hydrogen sulfide to be described subsequently.

The hydrocarbon phases from the two decanters 107 and 109 are led off by lines 116 and 117, expanded in the respective throttle valves 118 and 119, and combined for passage through the cooling coil or reflux condenser of a rectifier column 120 in which the combined hydrocarbons are introduced into a liquid/gas separator 121.

The gases generated by heating are fed via line 122 with the gas stream drawn into the ejector 105 for compression therein. The liquid phase from separator 121 is fed to the rectifier column 120 where it is transformed into a head fraction rich in hydrogen sulfide and into a heavy hydrocarbon sump fraction.

The sump fraction is drawn by line 123 and is further processed in a manner to be described below. The head fraction is delivered by line 124 to the liquid/gas separator 125 which has been mentioned previously.

The gas phases from the two decanters 107 and 109 are combined and fed by a line 126 into the rectifier column 106.

In the rectifier column 106 the removal of the $C_{4+}$ hydrocarbons is effected in the manner previously described. Thus a gas mixture substantially free from $C_{4+}$ hydrocarbons is withdrawn as the head product from the column 106 and is fed to a first scrubbing column 128.

The first scrubbing liquid for the latter column is dialkyl ether of a polyethylene glycol and is sprayed via line 129 into the head of the scrubber 128 in which it trickles downwardly past the plates or bottoms in counterflow to the gas stream from which practically all of the hydrogen sulfide is removed.

The charged scrubbing liquid is withdrawn from the sump of the column 128 and is expanded in the liquid turbine 130 before being delivered to the separator 125.

The separator 125 is provided with a packing 125a to ensure intimate contact between the liquid and the gas so that further hydrogen sulfide is solubilized from the gas phase. Simultaneously dissolved hydrocarbons are driven off and are withdrawn via line 131 for delivery to the ejector 105 and compression therein as previously discussed.

The liquid from separator 125 is fed via line 132 to a throttle valve 133 at which it is expanded and fed to a liquid/gas separator. The gaseous hydrogen sulfide thus released is expanded through throttle valve 135 and is withdrawn from the system via line 136, e.g. as product hydrogen sulfide which can serve as the feed to a Claus plant.

The liquid phase from separator 134 is expanded through throttle valve 137 and is heated by passage through heat exchangers 138 and 139 (the latter receiving heat from a foreign source) before being fed to a packed column 140 in which the downwardly trickling charged scrubbing liquid is contacted with a stripping gas delivered by line 141 and consisting predominantly of $CO_2$. The liquid phase is thereby substantially completely freed from the $H_2S$ which passes to line 136 previously mentioned.

The regenerated scrubbing liquid is cooled in the heat exchanger 138 by indirect heat exchange with the expanded liquid phase from separator 134, and is pumped at 142 through line 129 to the head of the first scrubber 128 at the pressure thereof.

The combined gas from the head of the packed column 140 and from the separator 134 which is discharged at line 136 as the product gas has a high concentration of hydrogen sulfide which is particularly desirable for use in a Claus plant for conversion to elemental sulfur.

The head product of the first scrubber 128 is fed by line 143 to a sump-heated, head-cooled, rectifying column 144 operated under pressure and in which $C_3$ hydrocarbons are removed from the gas.

The gases freed from $C_3$ hydrocarbons, withdrawn as the head product of the rectifier column 144 are fed via line 145 to the lower portion of a second scrubber 146 in which the gas is scrubbed with methanol sprayed into the head of the column via line 147 and trickling downwardly through the plates or bottoms thereof. The second scrubbing liquid used in this column entrains the carbon dioxide therewith and thus removes the carbon dioxide from the gas.

Substantially pure methane is withdrawn through line 148 as product gas from the head of column 146 and is passed through the heat exchanger 104 in indirect heat exchange with the raw gas. It is fed via line 149 to the pipeline.

The $CO_2$-charged methanol is drawn from the sump of the second scrubber 146 and is expanded in a liquid turbine 150 before it enters a liquid/gas separator 151. The released gas, consisting predominantly of methane but containing a substantial amount of carbon dioxide as an impurity, is discharged at 152 and can serve as a heating gas for the heat requirements of the process.

The liquid phase from separator 151 is expanded through a throttle valve 153 and introduced into a liquid/gas separator 154 from which the liquid phase, expanded through a throttle 155, is fed to a liquid/gas separator 156. A final expansion of the liquid phase from the latter separator is effected through a throttle valve 157 before entering the liquid/gas separator 158 from which regenerated methanol is withdrawn by a pump 159, pressurized therein to the pressure in the second scrubber 146, and fed by line 147 to the latter.

The gases at various pressures drawn off from the separators 154, 156 and 158 are pressurized in compressors 160, 161 and 162 to various pressures and, for example, the compressor 160 can deliver high-purity $CO_2$ as a product at line 163 at which this product is mixed with the head product from a rectifier column 167 described subsequently. The input to compressor 160 derives from the liquid/gas separator 154 and the compressor 161 which, in turn, receives gas from the separator 156 and a compressor 162 drawing upon the gas separated at 158.

A portion of the high carbon dioxide gas upstream of the compressor 161 is branched to line 141 as the stripping gas fed to the packed column 140.

The sump product from the rectifier column 144 is drawn off via line 165 and is expanded through throttle valve 166 before being fed to the rectifier column 167 which is provided with sump-heating and head-cooling elements as shown.

High-purity carbon dioxide is drawn off as the head product from column 167 and is combined, via line 168, with the $CO_2$ from compressor 160 before it is delivered to line 163. THe carbon dioxide product can be liquefied for used in the food industry or for any other conventional purpose.

The sump product of rectifier column 167 is combined with the sump product removed by line 123 from the rectifier column 120 and is fed to a unit 169 at which, as described for the unit 41, hydrogenation and desulfurization are carried out.

In this unit $C_3$–$C_{5+}$ hydrocarbons and organic sulfur compounds are hydrogenated to transform the sulfur to hydrogen sulfide. Hydrogen is supplied at 170 and the hydrogen sulfide removed at 171.

The remaining hydrogen mixture is fed to a sump-heated and head-cooled rectifier column 172.

From the head of this latter column a mixture of inert gases is withdrawn via line 173 and can be vented into the atmosphere. The higher hydrocarbons which collect in the sump are withdrawn, expanded through throttle 174 and fed to a further rectification column 175 provided with sump-heating and head-cooling means.

From the sump a mixture of $C_{5+}$ hydrocarbons is withdrawn via line 177 while a mixture of $C_3$ and $C_4$ is recovered from the head of column 175 via line 176 and can be used commercially wherever liquefied gas is required.

We claim:

1. A method of separating components from a raw natural gas containing methane, hydrogen sulfide, higher hydrocarbons and possibly organosulfur compounds and carbonyl sulfide, which comprises the steps of:
   (a) removing a higher hydrocarbon fraction from said raw gas which includes hydrocarbons with a carbon number of 4 and greater;
   (b) selectively scrubbing hydrogen sulfide with a first regeneratable scrubbing liquid from the raw gas subsequent to its treatment in step (a);
   (c) thereafter removing a $C_3$-hydrocarbon fraction from the raw gas from which hydrogen sulfide has been scrubbed in step (b); and
   (d) selectively scrubbing the gas from which the $C_3$-hydrocarbon fraction has been removed in step (c) with a separate second regeneratable scrubbing liquid to remove $CO_2$, thereby yielding a gas consisting predominantly of methane.

2. The method defined in claim 1 wherein said first scrubbing liquid is selected from the group which consists of dialkyl ethers of polyethylene glycols.

3. The method defined in claim 1 wherein said second scrubbing liquid is an alcohol.

4. The method defined in claim 3 wherein said second scrubbing liquid is a methanol.

5. The method defined in claim 1, claim 2, claim 3 or claim 4 wherein at least one of the hydrocarbon separations of steps (a) and (c) is carried out at least in part by condensation of the hydrocarbons in the gas.

6. The method defined in claim 1, claim 2, claim 3 or claim 4 wherein at least one of the hydrocarbon separations of steps (a) and (c) is carried out at least in part by rectification of the gas.

7. The method defined in claim 1, claim 3 or claim 4 wherein at least one of the hydrocarbon fractions separated in step (a) or (c) is hydrogenated to transform any original sulfur compounds therein to hydrogen sulfide in the resulting hydrogenated mixture.

8. The method defined in claim 7, further comprising the step of separating said hydrogenated mixture into a hydrogen sulfide-rich fraction and a plurality of low-sulfur hydrocarbon fractions; and circulating the hydrogen sulfide-rich fraction to step (b), for scrubbing with said first scrubbing liquid.

9. The method defined in claim 1, claim 3, claim 4 or claim 5 wherein the hydrocarbon separation in step (a) is carried out at least in part by a low-temperature condensation of the hydrocarbon fraction, and the hydrocarbon separation in step (c) is carried out by treating the gas therein with a separate third regeneratable scrubbing liquid.

10. The method defined in claim 9 wherein said third scrubbing liquid is a mixture of hydrocarbons.

11. The method defined in claim 10 wherein said third scrubbing liquid is a gasoline cut containing $C_7$ to $C_{11}$ hydrocarbons.

12. The method defined in claim 9, further comprising the steps of:
   ($b_1$) expanding the charged first scrubbing liquid from step (b) to release gas therefrom; and
   ($b_2$) afterscrubbing the released gas with a portion of first scrubbing liquid.

13. The method defined in claim 12 wherein the gas subsequent to step ($b_2$) is subjected to:
   ($b_3$) a second afterscrubbing with the third scrubbing liquid.

14. The method defined in claim 1 wherein step (c) is carried out by scrubbing the gas with a separate third scrubbing liquid capable of removing said $C_3$ hydrocarbons from the gas, said method further comprising the steps of:
   ($c_1$) expanding said third scrubbing liquid to release a gas therefrom; and
   ($c_2$) afterscrubbing the gas released in step ($c_1$) with a portion of said third scrubbing liquid.

15. The method defined in claim 14, further comprising the step of:
   ($c_3$) expanding said portion of said third scrubbing liquid following step ($c_2$) and heating said portion of said third scrubbing liquid to regenerate the same.

16. The method defined in claim 15, further comprising the step of:
   ($c_4$) expanding gases released during the regeneration of said third scrubbing liquid, partly liquefying the compressed gases and recovering a gaseous carbon dioxide fraction and a liquid fraction thereof, the latter liquid fraction containing $C_3$ hydrocarbons and organosulfur compounds.

17. The method defined in claim 1, further comprising the steps of:
   ($d_1$) expanding the charged second scrubbing liquid of step (d) and releasing gas therefrom by such expansion; and
   ($d_2$) combining the gas released in step ($d_1$) with a gas obtained after an afterscrubbing of a liquid used in scrubbing gas in step (c) and compressing the resulting mixture before scrubing same with the second scrubbing liquid.

18. The method defined in claim 1 whereby said second scrubbing liquid is regenerated to release carbon dioxide which is combined with carbon dioxide generated by the regeneration of a separate third scrubbing liquid used in step (c).

* * * * *